(12) United States Patent
Chu et al.

(10) Patent No.: US 11,772,053 B2
(45) Date of Patent: Oct. 3, 2023

(54) CARBON MOLECULAR SIEVE MEMBRANES CONTAINING A GROUP 13 METAL AND METHOD TO MAKE THEM

(71) Applicants: Dow Global Technologies LLC, Midland, MI (US); Georgia Tech Research Corporation, Atlanta, GA (US)

(72) Inventors: Yu-Han Chu, Beaverton, OR (US); William J. Koros, Atlanta, GA (US); Liren Xu, Freeport, TX (US); Mark K. Brayden, Plaquemine, LA (US); Marcos V. Martinez, Freeport, TX (US)

(73) Assignees: Dow Global Technologies LLC, Midland, MI (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 17/974,786

(22) Filed: Oct. 27, 2022

(65) Prior Publication Data

US 2023/0088542 A1 Mar. 23, 2023

Related U.S. Application Data

(63) Continuation of application No. 16/758,114, filed as application No. PCT/US2018/036597 on Jun. 8, 2018, now Pat. No. 11,504,675.

(60) Provisional application No. 62/578,558, filed on Oct. 30, 2017.

(51) Int. Cl.
| | | |
|---|---|---|
| *B01D 53/22* | (2006.01) | |
| *B01D 71/02* | (2006.01) | |
| *B01D 67/00* | (2006.01) | |
| *B01D 69/14* | (2006.01) | |

(52) U.S. Cl.
CPC ......... *B01D 71/021* (2013.01); *B01D 53/228* (2013.01); *B01D 67/0067* (2013.01); *B01D 67/0076* (2013.01); *B01D 69/141* (2013.01); *B01D 71/022* (2013.01); *B01D 67/0011* (2013.01)

(58) Field of Classification Search
CPC .............. B01D 67/0076; B01D 53/228; B01D 67/0067; B01D 71/021; B01D 71/022; B01D 67/0011; B01D 69/141
See application file for complete search history.

(56) References Cited

U.S. PATENT DOCUMENTS

| | | | |
|---|---|---|---|
| 3,179,500 A | 4/1965 | Bowen et al. | |
| 3,791,959 A | 2/1974 | Mills et al. | |
| 4,315,819 A | 2/1982 | King et al. | |
| 5,288,304 A | 2/1994 | Koros et al. | |
| 5,474,681 A * | 12/1995 | Fehlner | B01D 71/028 210/500.25 |
| 5,618,435 A * | 4/1997 | Fehlner | B01D 67/0083 210/651 |
| 5,779,904 A * | 7/1998 | Ruderman | B01J 37/0246 427/244 |
| 5,980,855 A * | 11/1999 | Shackle | B01J 31/0208 423/179.5 |
| 6,051,339 A * | 4/2000 | Shackle | C01G 31/00 423/306 |
| 6,471,745 B1 | 10/2002 | Foley et al. | |
| 6,565,631 B2 | 5/2003 | Koros et al. | |
| 8,486,179 B2 | 7/2013 | Willmott | |
| 8,709,133 B2 | 4/2014 | Kiyono et al. | |
| 8,911,534 B2 | 12/2014 | Koros et al. | |
| 2003/0147801 A1 | 8/2003 | Someya et al. | |
| 2004/0234566 A1 | 11/2004 | Qiu et al. | |
| 2006/0073080 A1 | 4/2006 | Fonkovich et al. | |
| 2007/0225532 A1 | 9/2007 | Fonkovich et al. | |
| 2007/0256736 A1 | 11/2007 | Fonkovich et al. | |
| 2009/0130704 A1* | 5/2009 | Gyure | C12M 39/00 435/292.1 |
| 2010/0081726 A1 | 4/2010 | Fonkovich et al. | |
| 2010/0300114 A1 | 12/2010 | Mhadeshwar et al. | |
| 2013/0319022 A1 | 12/2013 | Becze et al. | |

(Continued)

FOREIGN PATENT DOCUMENTS

| | | |
|---|---|---|
| CN | 102527256 A | 7/2017 |
| EP | 0459623 A1 | 12/1991 |

(Continued)

OTHER PUBLICATIONS

Communication Pursuant to Rules 161(1) and 162 EPC, dated Jun. 16, 2020, pertaining to EP 18735086.3.

Yoshimune M. et al.: "Gas transport properties of carbon molecular sieve membranes derived from metal containing sulfonated poly(phenylene oxide)", Desalination, Elsevier, Amsterdam, NL, vol. 193, No. 1-3, May 10, 2006 (May 10, 2006), pp. 66-72.

(Continued)

*Primary Examiner* — Anthony R Shumate
(74) *Attorney, Agent, or Firm* — Dinsmore & Shohl LLP

(57) ABSTRACT

A carbon molecular sieve (CMS) membrane having improved separation characteristics for separating olefins from their corresponding paraffins is comprised of carbon with at most trace amounts of sulfur and a group 13 metal. The CMS membrane may be made by pyrolyzing a precursor polymer devoid of sulfur in which the precursor polymer has had a group 13 metal incorporated into it, wherein the metal is in a reduced state. The pyrolyzing for the precursor having the group 13 metal incorporated into it is performed in a nonoxidizing atmosphere and at a heating rate and temperature such that the metal in a reduced state (e.g., covalently bonded to carbon or nitrogen or in the metal state).

14 Claims, No Drawings

(56) References Cited

U.S. PATENT DOCUMENTS

| | | | |
|---|---|---|---|
| 2015/0053079 A1* | 2/2015 | Koros | B29D 22/00 |
| | | | 264/176.1 |
| 2015/0094445 A1 | 4/2015 | Bhuwania et al. | |
| 2016/0245125 A1 | 8/2016 | Watkins | |
| 2016/0256818 A1 | 9/2016 | Gerber | |
| 2016/0263534 A1 | 9/2016 | Ferraris et al. | |
| 2017/0120200 A1* | 5/2017 | Lee | B01D 67/0067 |
| 2018/0008937 A1* | 1/2018 | Hong | B01D 71/025 |
| 2018/0015421 A1* | 1/2018 | Curulla-Ferre | B01D 69/04 |
| 2019/0060835 A1* | 2/2019 | Ding | B01D 71/48 |
| 2019/0118133 A1 | 4/2019 | Chu et al. | |
| 2021/0129085 A1* | 5/2021 | Xu | B01D 67/0067 |
| 2022/0241732 A1* | 8/2022 | Liu | B01D 71/027 |

FOREIGN PATENT DOCUMENTS

| | | | |
|---|---|---|---|
| JP | 2007196185 A | 8/2007 | |
| JP | 2010269229 A | 12/2010 | |
| WO | 2013165866 A1 | 11/2013 | |
| WO | 2015048754 A1 | 4/2015 | |
| WO | 2016048479 A1 | 3/2016 | |

OTHER PUBLICATIONS

Liao Kuo-Sung et al.: "Boron-embedded hydrolyzed PIM-1 carbon membranes for synergistic ethylene/ethane purification", Journal of Membrane Science, vol. 534, pp. 92-99.
Zhong D H et al.: "Effect of low-level boron doping on oxidation behavior of polyimide-derived carbon films", Car, Elsevier, Oxford, GB, vol. 38, No. 8, Jan. 1, 2000 (Jan. 1, 2000), pp. 1199-1206.
Konno H et al.: "Carbonization of boron containing polyimide films—B—N bond formation -", Carbon, Elsevier, Oxford, GB, vol. 37, No. 6, Jan. 1, 1999 (Jan. 1, 1999), pp. 887-895.
International Preliminary Report on Patentability, dated May 5, 2020, pertaining to PCT/US2018/036597.
International Search Report and Written Opinion, dated Sep. 3, 2020, pertaining to PCT/US2018/036597.
K. M. Steel and W. J. Koros, Investigation of Porosity of Carbon Materials and Related Effects on Gas Separation Properties, Carbon, 41, 253 (2003).
H. Suda and K. Haraya, Gas Permeation Through Micropores of Carbon Molecular Sieve Membranes Derived From Kapton Polyimide, J. Phys. Chem. B, 101, 3988 (1997).
V. C. Geiszler and W. J. Koros, Effects of Polyimide Pyrolysis Atmosphere on Separation Performance of Carbon Molecular Sieve Membranes, Ind. Eng. Chem. Res., (1996).
Xu et al., Journal of Membrane Science, 423-424, 2012, 314-323.
Bloch et al., Science, 335, 2012, 1606-1610.
Bloch et al., Journal of the American Chemical Society, 133, 2011, 14814-14822.
Teixeira et al., Chem Eng. Res. Des. 90 (2012) 2338-2345.
Barsema et al., Journal of Membrane Science, 219 (2003), 47-57.
Geier et al., Chemical Science, 2013, 4, 2054-2061.
Koresh et al., Atomic Energy Commission Nuclear Research Centre, Beer-Sheva, Israel, 1983, 723-734.
Los Alamos "Periodic Table of Elements", retrieved Oct. 26, 2022, p. 1, https://periodic.lanl.gov/index.shtml (Year: 2022).
Chinese Office Action Pertaining to Application No. 201880067597.8, dated Nov. 30, 2021.
Search Report pertaining to Application No. 201880067597.8, dated Nov. 30, 2021.
Communication pursuant to Article 94(3) EPC, pertaining to European Patent Application No. 18735086.2 dated Feb. 3, 2022 9 pages.
Chinese Office Action Pertaining to Application No. 201880067597.8, dated May 7, 2022 4 pages.
Search Report pertaining to Application No. 201880067597.8, dated May 7, 2022 4 pages.
Japanese Office Action pertaining to Application No. 2020-521950 dated Feb. 8, 2022.
Communication pursuant to Article 94(e) dated Dec. 12, 2022, pertaining to European Patent Application No. 18735086.3 DOW 81117 EP (7 pages).

* cited by examiner

CARBON MOLECULAR SIEVE MEMBRANES CONTAINING A GROUP 13 METAL AND METHOD TO MAKE THEM

CROSS REFERENCE TO RELATED APPLICATIONS

This application is a Continuation Application of U.S. patent application Ser. No. 16/758,114 filed on Apr. 22, 2020, which is a National Stage Entry of International Patent Application PCT/US2018/036597, filed Jun. 8, 2018, which claims priority to U.S. Provisional Application Ser. No. 62/578,558, filed on Oct. 30, 2017, the entire disclosures of which are incorporated by reference herein.

TECHNICAL FIELD

The invention relates to carbon molecular sieve (CMS) membranes for use in gas separation. In particular the invention relates to a method for producing CMS membranes with improved selectivity, permeability and stability.

BACKGROUND

Membranes are widely used for the separation of gases and liquids, including for example, separating acid gases, such as $CO_2$ and $H_2S$ from natural gas, and the removal of $O_2$ from air. Gas transport through such membranes is commonly modeled by the sorption-diffusion mechanism. Polymeric membranes have been well studied and are widely available for gaseous separations due to easy process-ability and low cost. CMS membranes, however, have been shown to have attractive separation performance properties exceeding that of polymeric membranes.

CMS membranes are typically produced through thermal pyrolysis of polymer precursors. For example, it is known that defect-free hollow fiber CMS membranes can be produced by pyrolyzing cellulose hollow fibers (J. E. Koresh and A. Soffer, Molecular sieve permselective membrane. Part I. Presentation of a new device for gas mixture separation. Separation Science and Technology, 18, 8 (1983)). In addition, many other polymers have been used to produce CMS membranes in fiber and dense film form, among which polyimides have been favored. Polyimides have a high glass transition temperature, are easy to process, and have one of the highest separation performance among other polymeric membranes, even prior to pyrolysis.

Polyimide hollow fibers have been pyrolyzed to form CMS membranes under vacuum such as described by U.S. Pat. No. 6,565,631. U.S. Pat. No. 6,565,631 also discloses a method of using CMS membranes to separate $CO_2$ from a methane stream containing 10% $CO_2$, at 1000 psia and 50° C., with a selectivity of approximately 45, a selectivity that is much higher than typical commercial polymeric membranes. Other patents that describe processes for producing carbon membranes (both asymmetric hollow "filamentary" and flat sheets), and applications for gas separation, include, for example, U.S. Pat. No. 5,288,304, and EP Patent No. 0459623.

To improve the separation properties of CMS membranes formed from polyimides research has focused primarily on a particular polyimide used and the conditions used to carbonize the particular polyimide. For example, Steel and Koros performed a detailed investigation of the impact of pyrolysis temperature, thermal soak time, and polymer composition on the performance of carbon membranes. (K. M. Steel and W. J. Koros, Investigation of Porosity of Carbon Materials and Related Effects on Gas Separation Properties, Carbon, 41, 253 (2003).) Membranes were produced in an air atmosphere at 0.05 mm Hg pressure. The results showed that increases in both temperature and thermal soak time increased the selectivity but decreased permeance for $CO_2$/$CH_4$ separation. In addition, Steel et al showed that a precursor polymer with a tightly packed structure tends to lead to a CMS membrane having higher selectivity compared with less compact precursor polymers.

The impact of pyrolysis atmosphere has been researched. Suda and Haraya disclosed the formation of CMS membranes under different environments. (H. Suda and K. Haraya, Gas Permeation Through Micropores of Carbon Molecular Sieve Membranes Derived From Kapton Polyimide, J. Phys. Chem. B, 101, 3988 (1997).) CMS dense films were prepared from polyimide Kapton® at 1000° C. in either argon or in vacuum. According to their gas separation properties, the results of an $O_2$/$N_2$ separation were almost the same between 6 membranes formed under the different atmospheres. Suda and Haraya did not disclose the effects of atmosphere on $CO_2$ separation from natural gas, nor disclose how separation properties vary with ability and low cost. Similarly, Geiszler and Koros disclosed the results of CMS fibers produced from pyrolysis of fluorinated polyimide in helium and argon for both $O_2$/$N_2$ and $H_2$/$N_2$ separations. (V. C. Geiszler and W. J. Koros, Effects of Polyimide Pyrolysis Atmosphere on Separation Performance of Carbon Molecular Sieve Membranes, Ind. Eng. Chem. Res., (1996)). That paper disclosed a slightly higher selectivity with vacuum pyrolysis than the purged pyrolysis processes. In addition, Geiszler and Koros showed that the flow rate of the purge gases impacted performance. In U.S. Pat. No. 8,486,179, the effect of using atmospheres having small amounts of oxygen in the pyrolysis atmosphere was described.

Limited research has been done on changing the chemistry of the polyimide such as incorporating metals that may have an affinity for particular gas molecules of interest (e.g., ethylene and propylene). Filler particles (clusters) of silver particles have been mixed in carbon membranes formed from P84 3,3'-4,4'-Benzophenone tetracarboxylic dianhydride-toluene diisocyanate/methylene diisocyanate (BTDA-TDI/MDI) copolyimide to separate He, $CO_2$, $O_2$ and $N_2$, has been described by J. N. Barsema et al., in J. Mem. Sci. 219 (2003) 47-57. Filler particles of alumina and silver were loaded into a carbonized phenolic resin for separating $C_3H_6$, $C_3H_8$, He, $N_2$, $CO_2$ and $O_2$ as described by M. Teixeira et al., Chem Eng. Res. Des. 90 (2012) 2338-2345. Particular metals such as silver, aluminum and copper have been incorporated into sulfonated polymers such as sulfonated poly(phenylene oxide) in which metals were formed upon carbonization of the sulfonated polymer to separate Hz, He, $N_2$, $CO_2$ and $O_2$, but the residual sulfur may be potentially poisonous as described by M. Yoshimune et al., in Desalination 193 (2006) 66-72.

It would be desirable to provide a CMS membrane and method to make the CMS membrane to improve the separation of particular gases such as olefins from paraffins and in particular propylene from ethane.

SUMMARY

A first aspect of the invention is a carbon molecular sieve membrane comprising, carbon with a group 13 metal and at most a trace amount of sulfur, wherein the group 13 metal is present in a reduced state. When referring to a group 13 metal, the group is as per IUPAC new notation (periodic table) as per *Handbook of Chemistry and Physics, 66th Ed.*, CRC Press Inc. (1985).

A second aspect is a process for separating a gas molecule from a feed gas comprised of the gas molecule and at least one other gas molecule comprising
 (i) providing the carbon molecular sieve membrane of the first aspect; and
 (ii) flowing the gas feed through and over said carbon molecular sieve membrane to produce a first permeate stream having an increased concentration of the gas molecule and a second retentate stream having a decreased concentration of the gas molecule. In a preferred embodiment, the gas feed is comprised of propylene and ethane, wherein the gas molecule is propylene and the other gas molecule is ethane.

A third aspect of the invention is a method of making a carbon molecular sieve membrane comprising,
 (i) providing a precursor polymer without any sulfur;
 (ii) incorporating a group 13 metal into the precursor polymer to form a group 13 metal bearing precursor polymer,
 (iii) heating said group 13 metal bearing precursor polymer to a final pyrolysis temperature and non-oxidizing atmosphere sufficient to form the carbon molecular sieve membrane containing the group 13 metal; and
 (iv) cooling the carbon molecular sieve membrane to room temperature.

and 5,5'-Methylene-bis(anthranilic acid) (MBAA)) that allow for the incorporation of the group 13 metal into the polyimide structure ionically. The polyimide may be a conventional or fluorinated polyimide. Desirable polyimides typically contain at least two different moieties selected from 2,4,6-trimethyl-1,3-phenylene diamine (DAM), oxydianaline (ODA), dimethyl-3,7-diaminodiphenyl-thiophene-5,5'-dioxide (DDBT), 3,5-diaminobenzoic acid (DABA), 2.3,5,6-tetramethyl-1,4-phenylene diamine (durene), meta-phenylenediamine (m-PDA), 2,4-diaminotolune (2,4-DAT), tetramethylmethylenedianaline (TMMDA), 5,5'-[2,2,2-trifluoro-1-(trifluoro-methyl)ethylidene]-1,3-isobenzofurandion (6FDA), 3,3',4,4'-biphenyl tetracarboxylic dianhydride (BPDA), pyromellitic dianhydride (PMDA), 1,4,5,8-naphthalene tetracarboxylic dianhydride (NTDA), and benzophenone tetracarboxylic dianhydride (BTDA), with two or more of 6FDA, BPDA and DAM being preferred.

An exemplary polyimide, designated as 6FDA/BPDA-DAM, may be synthesized via thermal or chemical processes from a combination of three monomers: DAM; 6FDA, and BPDA, each commercially available for example from Sigma-Aldrich Corporation. Formula 1 below shows a representative structure for 6FDA/BPDA-DAM, with a potential for adjusting the ratio between X and Y to tune polymer properties. As used in examples below, a 1:1 ratio of component X and component Y may also abbreviated as 6FDA/BPDA(1:1)-DAM.

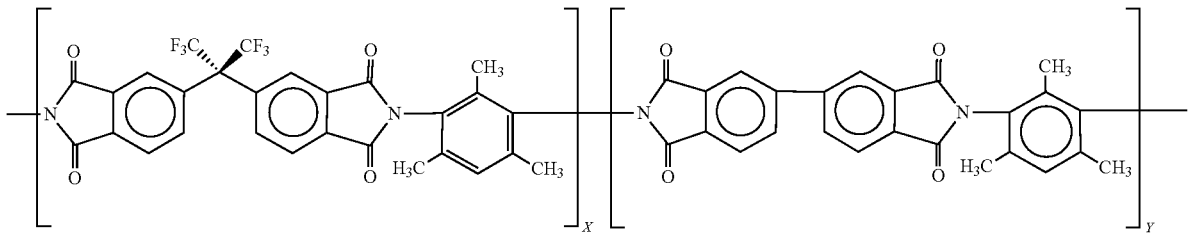

Formula 1. Chemical structure of 6FDA/BPDA-DAM

A fourth aspect of the invention is a carbon molecular sieve module comprising a sealable enclosure comprised of: a plurality of carbon molecular sieve membranes, comprising at least one carbon molecular sieve membrane of the first aspect, contained within the sealable enclosure; an inlet for introducing a gas feed comprised of at least two differing gas molecules; a first outlet for permitting egress of a permeate gas stream; and a second outlet for egress of a retentate gas stream.

The gas separation method is particularly useful for separating gas molecules in gas feeds that have very similar molecular sizes such as ethane/ethylene and propane/propylene and in particular propylene from ethane. It may also be used to separate other gases, for example separating oxygen from atmospheric air or separating gases (e.g., methane) in natural gas feeds.

Another exemplary polyimide, designated as 6FDA-DAM lacks BPDA such that Y equals zero in Formula 1 above. Formula 2 below shows a representative structure for this polyimide.

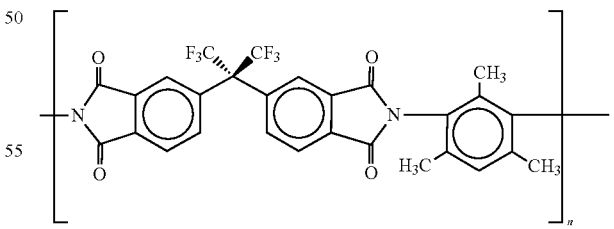

Formula 2. Chemical structure of 6FDA-DAM

DETAILED DESCRIPTION

The polyimide precursor polymer may be any polyimide polymer useful for making CMS membranes that does not contain sulfur and in which a group 13 metal may be added. In one embodiment, the polyimide contains moieties (e.g., polar moieties such as 3,5-diaminobenzoic acid (DABA)

A particularly useful polyimide for ionically incorporating a group 13 metal is 4,4'-hexafluoroisopropylidene diphthalic anhydride (6FDA), 2,4,6-trimethyl-1,3-phenylenediamine (DAM) and 3,5-diaminobenzoic acid (DABA) as shown below in Formula 3, and which may be abbreviated as 6FDA-DAM:DABA (3:2):

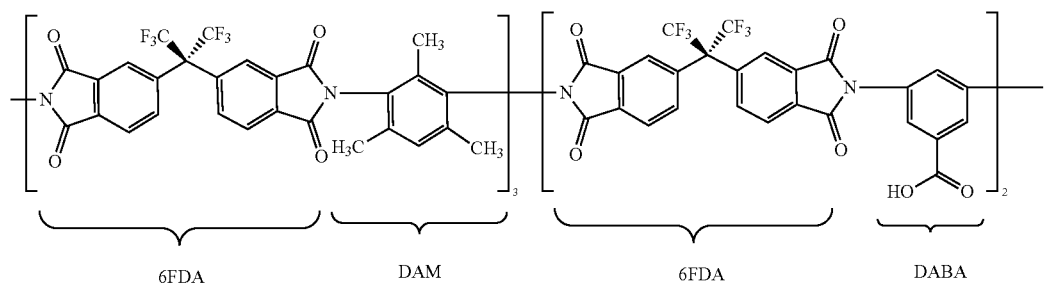

Formula 3. Chemical structure of 6FDA-DAM:DABA (3:2)

To realize a CMS membrane of the invention, a group 13 metal is incorporated into the precursor polymer to form a group 13 metal bearing precursor polymer. The incorporation may be by any useful method whereby the group 13 metal may be incorporated into the polyimide. It is desirable that the group 13 metal is incorporated in the polyimide on a fine scale. The group 13 metal may be incorporated by physical mixing or blending. For example, the polymer and a group 13 metal salt may be dissolved in a solvent, mixed and the solvent removed. In a particular embodiment a group 13 metal salt and a polyimide precursor having polar moieties are dissolved in a solvent and upon removal of the solvent with or without further heating, the salt decomposes and the group 13 metal ionically cross-links the polyimide polymer through the polar moieties. An example of such incorporation is illustrated as follows:

Incorporating the group 13 metal may also be achieved by infusing. For example, the metal may be incorporated into a solid polymer precursor by infusing a metal compound dissolved in a solvent (e.g., water, ethanol, methanol, hexane, $HCF_3$, and supercritical $CO_2$). An example of a metal compound useful to infuse or incorporate during the synthesis of the polyimide, other than those previously mentioned, is a metallocene such as ferrocene.

The group 13 metal salt may be any salt useful for incorporating into the polyimide, but typically is an organic salt such as a group 13 metal acetylacetonate, metal acetate, or metal chloride. Mixtures of differing salts as well as differing group 13 metals may be used.

The group 13 metal is as defined above. Preferably, the group 13 metal is boron or aluminum and most preferably aluminum. The Group 13 metal is present in the CMS

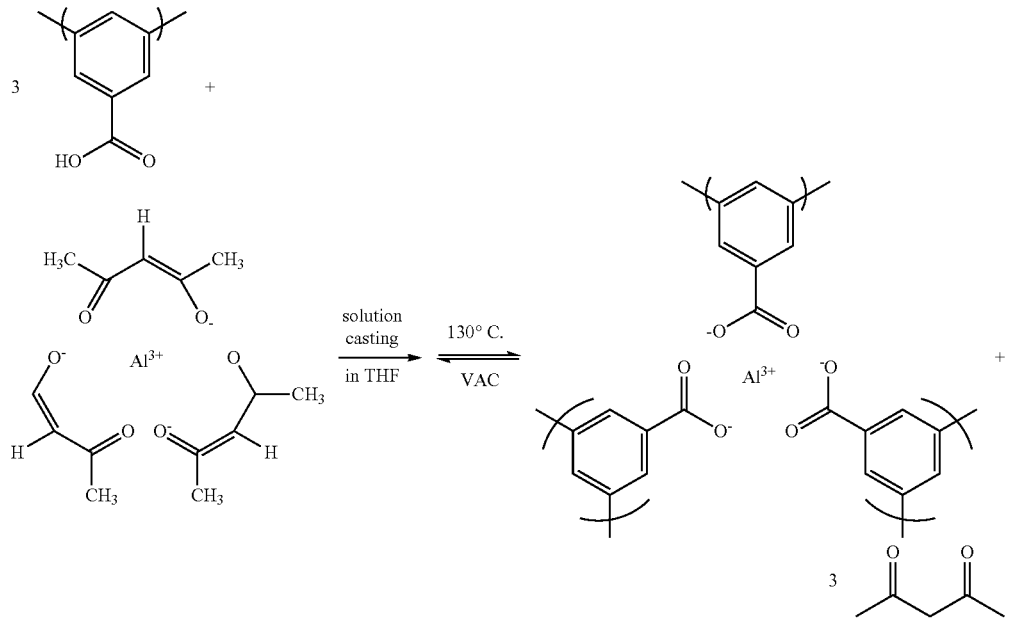

Group 13 metals may also be incorporated during the polyimide synthesis process. For example, a group 13 metal salt is added to a solution of polyamic acid having polar moieties, and the mixture is cast into a film. As the film is thermally cured at high temperature, the polyamic acid converts to polyimide and the metal ions react with the polar moieties to form an ionomer.

membrane in a reduced state such as a metal or covalently bonded to carbon or nitrogen and not as an oxide.

The amount of group 13 metal in the CMS membrane may be any amount useful to enhance the combination of permeance and selectivity of the desired gas molecule to be separated (e.g., propylene from ethane). Generally, the amount of group 13 metal is from 0.01% to 15% by weight of the CMS membrane. Desirably, the amount of group 13 metal is at least about 0.1%, 0.5%, or 1% to 12%, 10% or 8% by weight of the CMS membrane.

In forming the CMS membranes, the polyimides incorporating the group 13 metal are formed into hollow fiber membranes or film membranes. These as formed membranes (i.e., not yet pyrolyzed) are substantially defect-free. "Defect-free" means that selectivity of a gas pair, typically oxygen ($O_2$) and nitrogen ($N_2$), through a hollow fiber membrane or film membrane is at least 90 percent of the selectivity for the same gas pair through a dense film prepared from the same composition as that used to make the polymeric precursor hollow fiber membrane. By way of illustration, a 6FDA/BPDA(1:1)-DAM polymer has an intrinsic $O_2/N_2$ selectivity (also known as "dense film selectivity") of 4.1.

Conventional procedures to make the polyimide hollow fibers or films may be used. For example, coextrusion procedures including such as a dry-jet wet spinning process (in which an air gap exists between the tip of the spinneret and the coagulation or quench bath) or a wet spinning process (with zero air-gap distance) may be used to make the hollow fibers and solution casting may be used to make the films.

The particular heating rates, final pyrolysis temperatures, cooling rates and combinations of them are somewhat dependent on the particular polyimide, group 13 metal used and desired separations to be performed. Nevertheless, generally, it has been found particularly for separating olefins from their paraffin analogs and in particular propylene from ethane, that it is desirable to heat to the maximum pyrolysis temperature and hold at that temperature such that the group 13 metal tends to be reduced such that it is not present as an oxide. Generally, this tends to mean that is it is desirable to heat rapidly, hold for short times at lower maximum pyrolysis temperatures under non-oxidizing conditions (e.g., in the absence of any appreciable oxygen such as less than 100 ppm, but preferably no oxygen "less than 1 ppm").

Generally, the maximum or final pyrolysis temperature to carbonize the group 13 metal containing polyimide may be anywhere from 400 to 1000° C., but preferably is from about 500° C. to 700° C. or 600° C. The heating rate may be any suitable such as 1° C./minute to 100° C./minute, but desirably is from about 5° C./minute or 10° C./minute to 25° C./minute, or 20° C./minute. The amount of time at the final pyrolysis temperature is desirably from as short time practicable in view of the heating rate, e.g., several seconds or one minute to about 60 minutes. In an embodiment, the hold time at the final pyrolysis temperature is from 15 minutes to 60 minutes. Longer times tend not to be necessary and may negatively affect the desired combination of permeance and selectivity. Likewise, the cooling rate may be any suitable method such as merely passively cooling the furnace (by shutting the power off), but it may be desirable to cool rapidly or accelerate the cooling by a heat removal method.

Exemplary heat removal methods include: flowing a gas directly over the carbon molecular sieve membrane within the furnace; flowing a gas through the carbon molecular sieve membrane within the furnace; removing the furnace insulation; flowing a liquid over at least a portion of the furnace or flowing a gas over at least a portion of the furnace. Any one or combination of heat removal methods may be used, with it being desirable to have the cooling rate as high as possible at least from the final pyrolysis temperature to about 400° C. or to room temperature. Generally, the average cooling rate from the final pyrolysis temperature to 400° C. is at least about 2, 4 or 8° C./minute. The average heating rate is the temperature difference between the final pyrolysis temperature and 400° C. and the total time it takes to reach 400° C. The cooling rate from 400° C. to room temperature may be any practicable with faster being desirable merely for productivity sake.

It is understood that all temperatures, heating rates and cooling rates are those as measured in the furnace and not the actual CMS membranes being formed. The actual temperature of the CMS membranes being formed may vary somewhat due to temperature lag due to thermal mass within the furnace, particular furnace used and the like and is readily determinable by one skilled in the art.

Any suitable supporting means for holding the CMS membranes may be used during the pyrolysis including sandwiching between two metallic wire meshes or using a stainless steel mesh plate in combination with stainless steel wires and as described by U.S. Pat. No. 8,709,133 at col. 6, line 58 to col. 7, line 4, which is incorporated by reference. A quartz plate may be desirably used when supporting a dense film as opposed to a hollow fiber.

The group 13 metal containing polyimide may be carbonized under various inert gas purge or vacuum conditions, preferably under inert gas purge conditions, for the vacuum pyrolysis, preferably at low pressures (e.g. less than 0.1 millibar). In one embodiment the pyrolysis utilizes a controlled purge gas atmosphere during pyrolysis in which low levels of oxygen are present in an inert gas. By way of example, an inert gas such as argon is used as the purge gas atmosphere. Other suitable inert gases include, but are not limited to, nitrogen, helium, or any combinations thereof. By using any suitable method such as a valve, the inert gas containing a specific concentration of oxygen may be introduced into the pyrolysis atmosphere. For example, the amount of oxygen in the purge atmosphere may be less than about 50 ppm (parts per million) $O_2$/Ar. Alternatively, the amount of oxygen in the purge atmosphere may be less than 40 ppm $O_2$/Ar. Embodiments include pyrolysis atmospheres with about 8 ppm, 7 ppm, or 4 ppm $O_2$/Ar, but it is preferred as described above to have essentially no oxygen (i.e., less than about 1 ppm of $O_2$).

The gas permeation properties of a membrane can be determined by gas permeation experiments. Two intrinsic properties have utility in evaluating separation performance of a membrane material: its "permeability," a measure of the membrane's intrinsic productivity; and its "selectivity," a measure of the membrane's separation efficiency. One typically determines "permeability" in Barrer (1 Barrer=$10^{-10}$ [$cm^3$ (STP) cm]/[$cm^2$ s cmHg], calculated as the flux ($n_i$) divided by the partial pressure difference between the membrane upstream and downstream ($\Delta p_i$), and multiplied by the thickness of the membrane (l).

$$P_i = \frac{n_i l}{\Delta p_i}$$

Another term, "permeance," is defined herein as productivity of asymmetric hollow fiber membranes and is typically measured in Gas Permeation Units (GPU) (1 GPU=$10^{-6}$ [$cm^3$ (STP)]/[$cm^2$ s cmHg]), determined by dividing permeability by effective membrane separation layer thickness.

$$\left(\frac{P_i}{l}\right) = \frac{n_i}{\Delta p_i}$$

Finally, "selectivity" is defined herein as the ability of one gas's permeability through the membrane or permeance relative to the same property of another gas. It is measured as a unitless ratio.

$$\alpha_{i/j} = \frac{P_i}{P_j} = \frac{(P_i/l)}{(P_j/l)}$$

In a particular embodiment, the CMS membrane produced by the method enables a carbon hollow fiber CMS membrane that has a permeance of at least 5 GPU for a target gas molecule (permeate) and a selectivity of at least 10 and a stability such that said permeance and selectivity varies less than 20% after being continuously separating a feed gas comprised of a retentate gas molecule and permeate gas molecule for 10 days. Desirably, the permeance and selectivity varies less than 15%, 10% or 5% after continuously separating a feed gas comprised of a retentate and permeate gas molecule pair for 10, 30 or 60 days. In particular embodiments the permeate/retentate gas molecule pairs may be ethylene/ethane, propylene/propane, butylene/butane, methane/carbon dioxide, methane/water, oxygen/nitrogen, and methane/hydrogen sulfide. Illustratively, the feed gas generally is comprised of at least 50% the permeate gas molecule (e.g., ethylene or propylene) and 25% of retentate gas molecule (e.g., ethane or propane).

In a particular embodiment the CMS membrane produced has a permeance of at least 10 GPU for propylene (permeate) and a selectivity of at least 35 propylene/propane. Desirably, in this embodiment the permeance is at least 12, 15 or even 18 GPU for propylene. Likewise, in this embodiment the selectivity is at least 40, 45 or even 50 for propylene/propane. In another particular embodiment, the CMS membrane produced has a permeance of at least 10 GPU for ethylene (permeate) and a selectivity of at least 6 ethylene/ethane. Desirably, in this embodiment the permeance is at least 15, 18 or even 20 GPU for ethylene. Likewise, in this embodiment the selectivity is at least 8, 10 or even 12 for ethylene/ethane. In a further embodiment, the CMS membrane produced has a permeance of at least 10 GPU for butylene (permeate) and a selectivity of at least 5 for butylene/butane. Desirably, in this embodiment the permeance is at least 20, 30 or even 40 GPU for butylene. Likewise, in this embodiment the selectivity is at least 10, 15 or even 30 for butylene/butane.

The CMS membranes are particularly suitable for separating gases that are similar in sizes such as described above and involve flowing a gas feed containing a desired gas molecule and at least one other gas molecule through the CMS membrane. The flowing results in a first stream have an increased concentration of the desired gas molecule and second stream having an increased concentration of the other gas molecule. The process may be utilized to separate any of the aforementioned gas pairs and in particular is suitable for separating ethylene from ethane, propylene from propane and in particular propylene from ethane. Likewise, the process exhibits the same stability as it relates to permeance and selectivity over time as described above. When practicing the process, the CMS membrane is desirably fabricated into a module comprising a sealable enclosure comprised of a plurality of carbon molecular sieve membranes that is comprised of at least one carbon molecular sieve membrane produced by the method of the invention that are contained within the sealable enclosure. The sealable enclosure having an inlet for introducing a gas feed comprised of at least two differing gas molecules; a first outlet for permitting egress of a permeate gas stream; and a second outlet for egress of a retentate gas stream.

EXAMPLES

Example 1

The CMS membranes were made using 6FDA-DAM:DABA (3:2) polymer. The 6FDA-DAM:DABA was acquired from Akron Polymer Systems, Inc., Akron, Ohio. The polymer was dried under vacuum at 110° C. overnight to remove moisture. The dried polymer was dissolved in tetrahydrofuran (THF, >99.9% purity, Sigma-Aldrich, St. Louis, Mo.) in a 40 ml vial (vial A) to form a 2 to 3 wt % polymer solution. Aluminum(III) acetylacetonate (Sigma-Aldrich, St. Louis, Mo.) was dissolved in THF in a 20 ml vial (vial B) to form a Al-containing solution. The two solutions were filtered with 0.20 micron PTFE filters respectively for removing impurity, and the Al-containing solution in vial B was added to vial A to form the Al-containing polymer dope for film casting. The compositions of the solutions are shown in Table 1.

Polymer dense films were prepared by casting the mixed solution into a Teflon casting dish inside a glove bag (Cole-Parmer, Vernon Hills, Ill.) at room temperature. The glove bag was then purged with nitrogen and allowed to saturate with THF by waiting at least 3 hours before casting. After at least 3 days, the vitrified films were removed from the bag and dried in a vacuum oven at 130° C. for 24 hours to remove residual solvent. The dried films having a thickness of about 80 microns were then cut into 0.75 inch diameter discs that were then pyrolyzed as described below. The discs were pyrolyzed to form the CMS membranes by placing the discs on a slotted quartz plate with spacing between each disc. The combination of the discs and quartz plate were placed into a quartz tube of a tube furnace. The films were pyrolyzed under an inert gas (argon flowing at a rate of 200 standard cubic centimeters per minute (sccm)). Prior to pyrolyzing the furnace was purged with inert gas to remove oxygen for a minimum of ten hours to reduce the oxygen level to less than 1 ppm. The films were heated at a ramp rate until reaching the final pyrolysis temperature as shown in Table 2 to form the final CMS membranes. The formed CMS membranes were all cooled passively (furnace shut off with the same inert gas flow maintained until the furnace was cooled to about room temperature, ~4-6 hours).

After cooling, the CMS membranes were masked in a dense film permeation cell by using impermeable aluminum tape and five-minute epoxy (3M™ Scotch-Weld™ Epoxy Adhesive DP110). The permeation cell was then placed in a constant-volume permeation system, and the system was stabilized at 35° C. For each permeation test, the entire system was evacuated for 18 hours. After evacuation, the upstream was pressurized with feed gas at about 50 pounds per square inch absolute pressure (psia) while the downstream was kept at vacuum. The pressure rise in a constant, known downstream volume was monitored by a pressure transducer and recorded over time by LabVIEW (National Instruments, Austin, Tex.) until a steady state was achieved.

Example 1 was evaluated for multiple-component olefins/paraffins mixture separation. The multicomponent feed contained 54.60 mol % ethylene, 17.00 mol % ethane, 15.10 mol % propylene, and 13.30 mol % propane. The separation characteristics of the CMS membrane of Example 1 for the multicomponent feed are shown in Table 3.

Table 3 also shows comparative examples prepared in the same manner as for Example 1 except that instead of the Aluminum(III) acetylacetonate, Iron(II) acetylacetonate (Sigma-Aldrich, St. Louis, Mo.) was used in Comparative Example 2 and Iron(III) acetylacetonate (Sigma-Aldrich, St. Louis, Mo.) was used for Comparative Example 3. Comparative Example 1 did not employ a metal. The same preparation, pyrolysis conditions and testing was utilized. Surprisingly, Example 1 has the highest propylene/ethane selectivity, which is critical for bulk commercial olefin/paraffin separations. Example 1 also shows high ethylene and propylene permeability.

TABLE 1

Casting Solution Formulation

|  | Solvent | Solute |
|---|---|---|
| Vial A | 20 ml THF | 0.5 g polymer |
| Vial B | 5 ml THF | 0.05 g aluminum(III) acetylacetonate |

TABLE 2

Pyrolysis Conditions

| Example | Temp (° C.) | Atmosphere (sccm/Ar) | Heating Rate (C./min) | Soak Time (min) |
|---|---|---|---|---|
| 1 | 550 | 200 | 10 | 0 |

TABLE 3

Separation Characteristics

| Example | C2"/C2 | C2"/C3 | C3"/C2 | C2"/C3" | C2" (Barrer) | C2 (Barrer) | C3" (Barrer) | C3 (Barrer) |
|---|---|---|---|---|---|---|---|---|
| 1 (Al(acac)3) | 2.03 | ND | 4.55 | 0.45 | 1141 | 565 | 2617 | ND |
| Comp 1 (No metal) | 3.30 ± 0.39 | 23.15 ± 6.38 | 3.05 ± 0.15 | 1.09 ± 0.18 | 1159.30 ± 100.71 | 354.65 ± 11.08 | 1101.46 ± 88.32 | 54.51 ± 10.57 |
| Comp 2 (Fe(acac)2) | 8.53 ± 0.47 | ND | 1.88 ± 0.18 | 4.61 ± 0.68 | 95.15 ± 30.56 | 11.64 ± 4.17 | 22.45 ± 9.06 | ND |
| Comp 3 (Fe(acac)3) | 5.79 | ND | 1.62 | 3.58 | 177 | 31 | 51 | ND |

C2" = ethylene; C2 = ethane; C3" = propylene; C3 = propane.
ND = Not determined, unavailable due to the test limitation of gas chromatography (GC)

The invention claimed is:

1. A process for separating a gas molecule from a feed gas comprised of the gas molecule and at least one other gas molecule, the process comprising:
   (i) providing a carbon molecular sieve membrane comprising, carbon, a group 13 metal, and at most a trace amount of sulfur, wherein the group 13 metal is present in a reduced state, and wherein the group 13 metal is present in an amount of 0.5% to 10% by weight of the carbon molecular sieve membrane; and
   (ii) flowing the gas feed through and over said carbon molecular sieve membrane to produce a first permeate stream having an increased concentration of the gas molecule and a second retentate stream having a decreased concentration of the gas molecule, wherein the gas molecule is propylene and the at least one other gas molecule comprises ethane, and wherein the carbon molecular sieve membrane has a permeance of propylene of at least 10 GPU.

2. The process of claim 1, wherein the gas feed comprises at least 50 mol. % propylene and at least 25 mol. % ethane.

3. The process of claim 1, wherein the group 13 metal is selected from boron, aluminum, and combinations thereof.

4. The process of claim 1, wherein the group 13 metal comprises aluminum.

5. The process of claim 1, wherein the group 13 metal comprise boron.

6. The process of claim 1, wherein the carbon molecular sieve membrane is a hollow fiber.

7. The process of claim 1, wherein the carbon molecular sieve membrane does not contain sulfur.

8. A process for separating a gas molecule from a feed gas comprised of the gas molecule and at least one other gas molecule, the process comprising:
   (i) providing a carbon molecular sieve membrane comprising, carbon, a group 13 metal, and at most a trace amount of sulfur, wherein the group 13 metal is present in a reduced state, and wherein the group 13 metal is present in an amount of 0.5% to 10% by weight of the carbon molecular sieve membrane; and
   (ii) flowing the gas feed through and over said carbon molecular sieve membrane to produce a first permeate stream having an increased concentration of the gas molecule and a second retentate stream having a decreased concentration of the gas molecule, wherein the gas molecule is propylene and the at least one other gas molecule comprises ethane, and wherein the gas feed comprises at least 50 mol. % propylene and at least 25 mol. % ethane.

9. The process of claim 8, wherein the carbon molecular sieve membrane has a permeance of propylene of at least 10 GPU.

10. The process of claim 8, wherein the group 13 metal is selected from boron, aluminum, and combinations thereof.

11. The process of claim 8, wherein the group 13 metal comprises aluminum.

12. The process of claim 8, wherein the group 13 metal comprise boron.

13. The process of claim 8, wherein the carbon molecular sieve membrane is a hollow fiber.

14. The process of claim 8, wherein the carbon molecular sieve membrane does not contain sulfur.

* * * * *